(12) United States Patent
Groop et al.

(10) Patent No.: US 11,213,665 B2
(45) Date of Patent: Jan. 4, 2022

(54) ANGLED MICRONEEDLE CARTRIDGE

(71) Applicant: Esthetic Education LLC, Scottsdale, AZ (US)

(72) Inventors: Kristin Groop, Scottsdale, AZ (US); Lawrence Groop, Scottsdale, AZ (US)

(73) Assignee: Esthetic Education LLC, Scottsdale, AZ (US)

( * ) Notice: Subject to any disclaimer, the term of this patent is extended or adjusted under 35 U.S.C. 154(b) by 70 days.

(21) Appl. No.: 16/438,180

(22) Filed: Jun. 11, 2019

(65) Prior Publication Data

US 2019/0381298 A1    Dec. 19, 2019

Related U.S. Application Data

(60) Provisional application No. 62/685,586, filed on Jun. 15, 2018.

(51) Int. Cl.
*A61M 37/00*    (2006.01)

(52) U.S. Cl.
CPC .............................. *A61M 37/0015* (2013.01)

(58) Field of Classification Search
CPC ......... A61M 37/0015; A61M 37/0076; A61M 2037/0023
See application file for complete search history.

(56) References Cited

U.S. PATENT DOCUMENTS

| | | | |
|---|---|---|---|
| 9,636,491 B1 * | 5/2017 | O'Brien, III | A61M 5/3297 |
| 2004/0116953 A1 * | 6/2004 | Dixon | A61M 37/0076 606/186 |
| 2009/0125050 A1 * | 5/2009 | Dixon | A61M 37/0076 606/186 |
| 2009/0216215 A1 * | 8/2009 | Thalmann | A61M 25/0612 604/506 |
| 2014/0088549 A1 * | 3/2014 | Cole | A61M 5/14248 604/506 |
| 2017/0281919 A1 * | 10/2017 | Asai | A61M 37/0015 |

\* cited by examiner

*Primary Examiner* — Deanna K Hall
(74) *Attorney, Agent, or Firm* — Joseph W Mott; Hartman Titus PLC

(57) ABSTRACT

A microneedling device includes a microneedle cartridge that extends needles at a predetermined angle, rather than perpendicular to the centerline of the device.

16 Claims, 3 Drawing Sheets

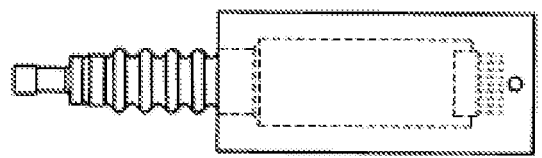
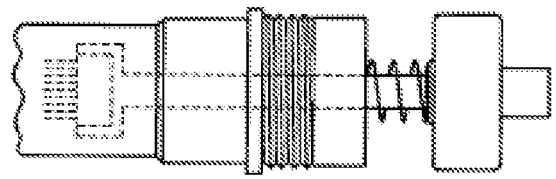
FIG. 1A    FIG. 1B
PRIOR ART
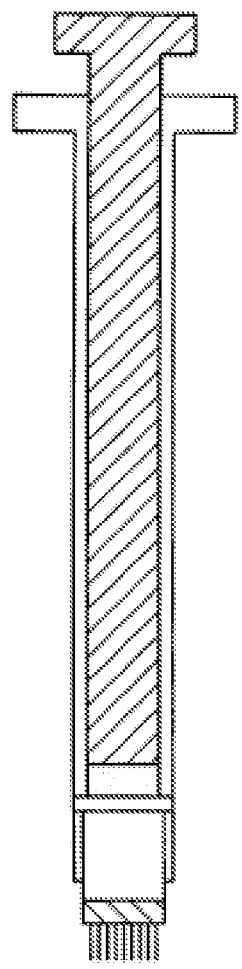
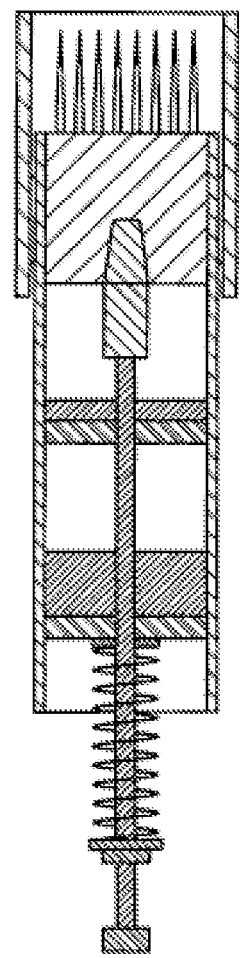
PRIOR ART
FIG. 1C    FIG. 1D

ANGLED MICRONEEDLE CARTRIDGE

CROSS REFERENCE TO RELATED APPLICATIONS

This application claims the benefit of priority of provisional patent application 62/685,586, filed Jun. 15, 2018.

TECHNICAL FIELD OF THE INVENTION

The present disclosure relates to an improvement in microneedling with particular application in treatment of burn related scarring of the skin.

BACKGROUND OF THE INVENTION

There are several peer-reviewed research articles that have been published exhibiting both the safety and efficacy of using microneedling devices to treat a wide range of skin conditions including age management (fine lines and wrinkles), dyschromias such as melasma, surgical scars, traumatic scars, acne scarring, striae, and alopecia. However, the scarring after significant burning of the skin poses a particular challenge to improve appearance and function.

The physiopathology of thermal skin injury involves significant fibrosis with contracture that inhibits function and causes significant pain for the patient. Additionally, the structure and function of the scar tissue that forms after burning the skin is different from that of skin that has been injured via non-thermal means. This is further complicated by skin grafting treatments.

Microneedling has been used to improve the function of hypertrophic scars as it mechanically breaks down tissue via rapid reciprocation of an array of sharp microneedles. However, the morphology of the hypertrophic tissue after to a deep burn can present challenges during microneedling treatment. While the hypertrophic tissue is thick, the lack of a healthy, normal deep dermis, and often a subcutaneous layer, can result in bleeding and pain when attempting to break up the hypertrophic tissue with current microdevice technology as the needle arrays are designed to propel the needles perpendicular to the skin surface.

If one were to change the angle of penetration from perpendicular to a more acute angle such as 75 degrees, more of the needle length and surface area would come into contact with the thick hypertrophic tissue on the top surface of a burn scar while subsequently not penetrating as deeply into the soft vascular tissue underneath the hypertrophic layer. However, in order for a microneedling device to function efficiently, the angle of insertion must be close to or equal to the angle of the drive rod. Tilting the device is undesirable because the angle is imprecise and the majority of the needles in the array will be flailing at the air above the skin.

In order to be able to microneedle burned skin at an angle such as 75 degrees from the surface plane of the skin with a microneedling device, one must construct a cartridge with a cartridge edge at 15 degrees while simultaneously angling the needle array plate and microneedles at 15 degrees.

By using the angled microneedling cartridge, the clinician can more efficiently break up the surface hypertrophic tissue of a burn scar while minimizing the damage caused to the underlying tissue.

SUMMARY OF THE INVENTION

A cartridge for attachment to a microneedling pen or device has an angled distal end with a defined predetermined angle. The microneedles in the cartridge extend at the same predetermined angle.

BRIEF DESCRIPTION OF THE DRAWINGS

FIGS. 1A-1D depict the structures of existing microneedle cartridges.

DETAILED DESCRIPTION

Figure 2:
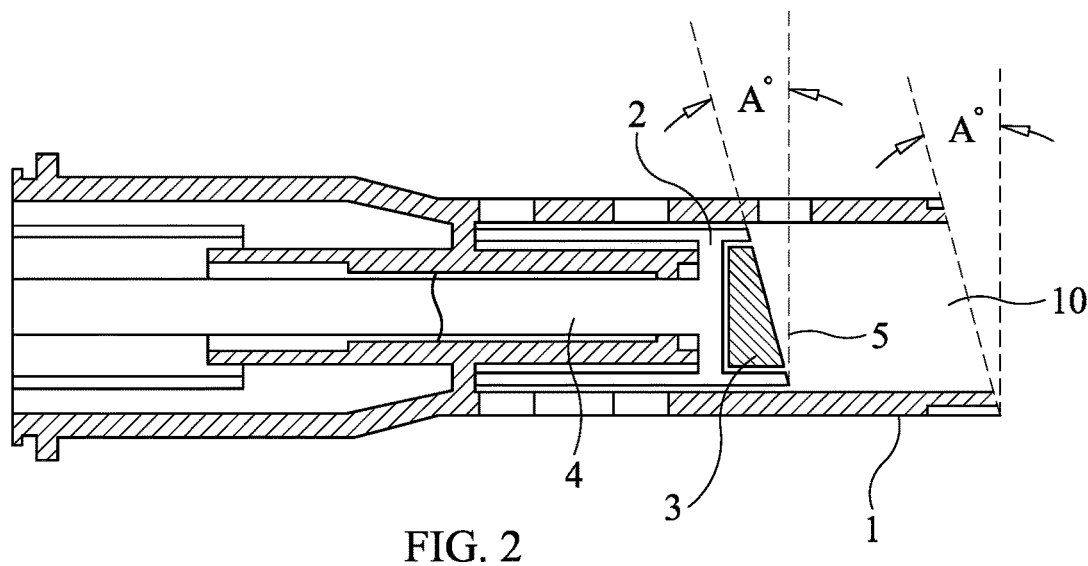
FIG. 2 shows an embodiment of an angled cartridge.

Microneedling devices used for skin treatment commonly include a cartridge casing (usually cylindrical) that protects and encloses a needle platform that itself supports and partially encloses a needle array plate. A drive rod rapidly reciprocates the platform through the casing, causing the needles to repeatedly penetrate the skin. Examples of available cartridges are shown in FIGS. 1A to 1D. To achieve a proper configuration for angled needles, both the cartridge casing and the array of needles should have corresponding orientation and must maintain that orientation consistently during operation As seen in FIG. 2, the distal end 10 of cylindrical cartridge casing 1 is formed at a predetermined angle A to the horizontal surface of the skin or surface to which it will be pressed. The complement of A (90 degrees minus A) is the angle relative to the axial centerline of the cartridge. Needle platform 2, attached to drive rod 4, has distal end 5 similarly formed at the same angle, to accommodate an angled needle array plate 3.

Figure 3:
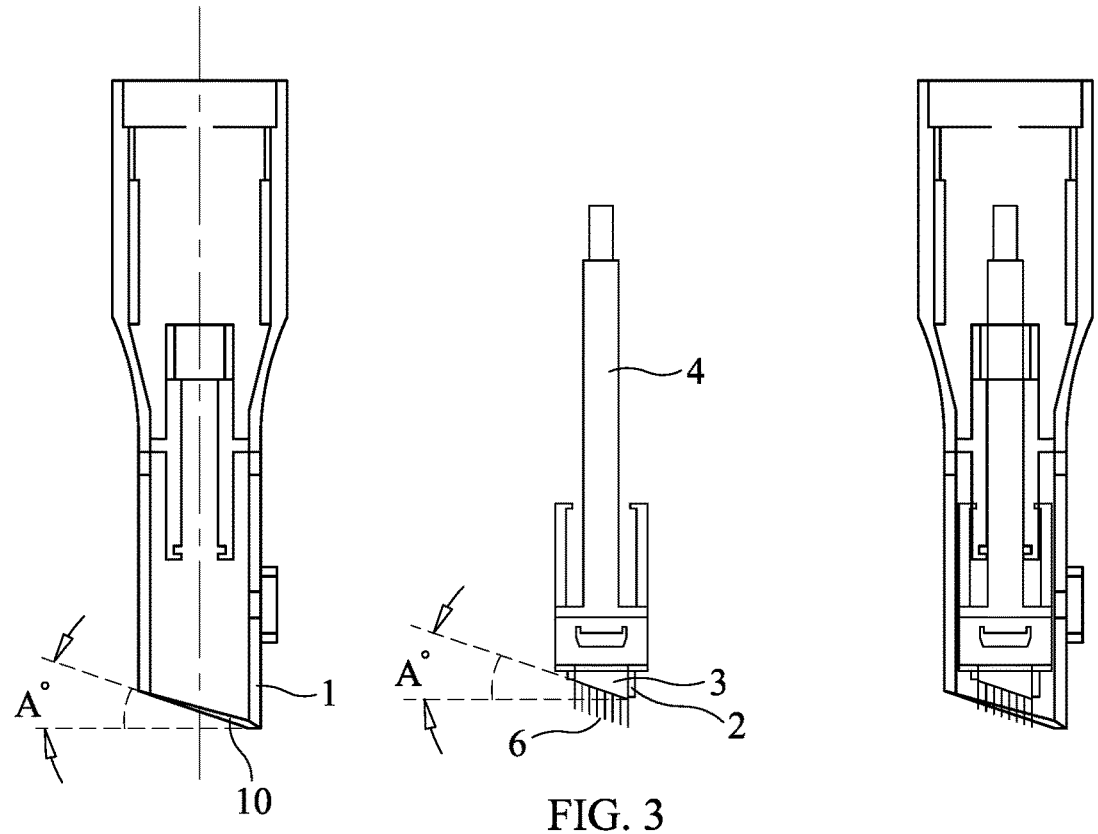
FIG. 3 shows an embodiment having a microneedle plate angled to conform with an angled cartridge.
Figure 4A:
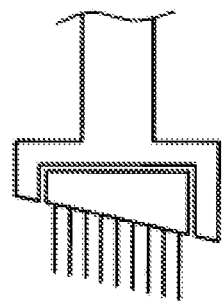
FIGS. 4A and 4B show alternative configurations for a portion of the embodiment of FIG. 3.
Figure 4B:
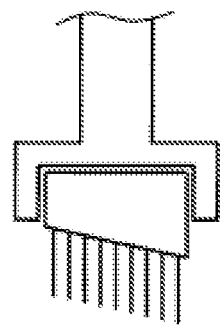

One way of configuring the cartridge assembly for an angled needle array is shown in FIG. 3. The distal end 10 of cartridge casing 1 has been made to a predetermined angle A from the horizontal. The needle platform 2 is conformed to the same angle, and the needle array plate 3 is as well. The needles themselves 6 are uniform length but the angled array plate and platform have the effect of an angled application on the skin surface. Angling the platform end in conformance with the angled needle array plate protects and secures the plate within the platform, as in FIG. 4A. It is also feasible to use a platform with a distal end that is perpendicular to the drive rod and insert an angled array plate, which will extend slightly beyond the end of the platform, as in FIG. 4B.

Figure 5:
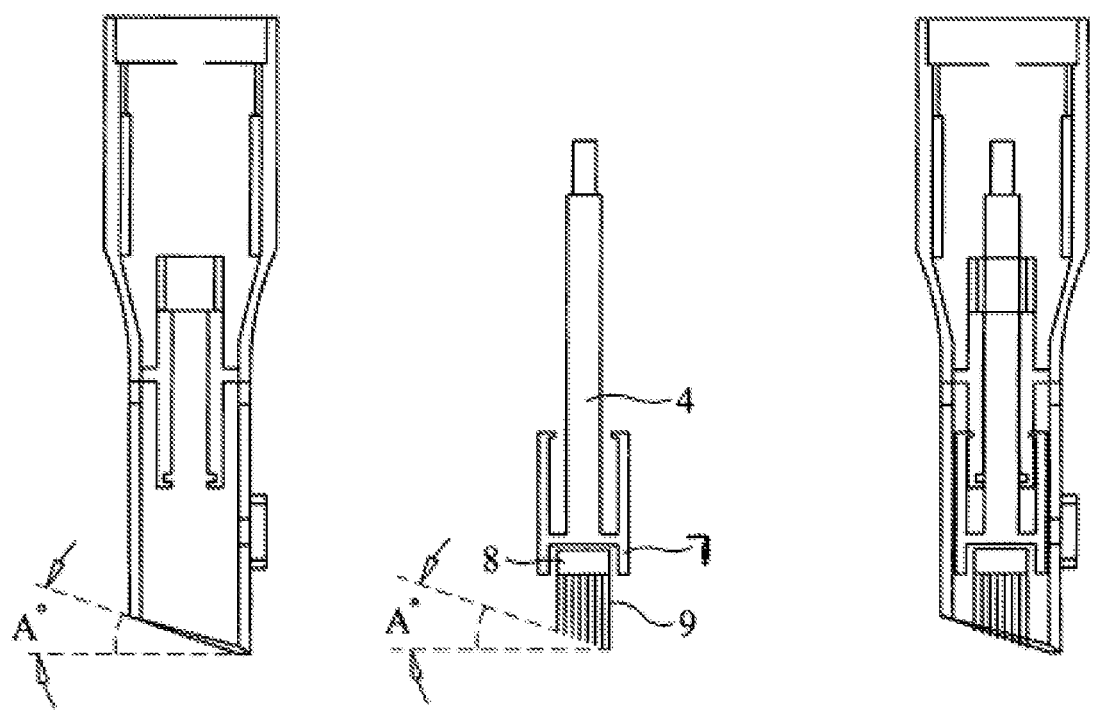
FIG. 5 shows an embodiment having a flat microneedle plate and graduated length needles.

Another possible configuration is shown in FIG. 5. Here the configuration of the cartridge casing is the same as the prior embodiment, but the needle platform 7 and the needle array plate 8 are set horizontal and the needles 9 are different lengths. The graduation from shorter to longer across the platform is set to the same attack angle A as present on the cartridge casing.

Experimentation has shown that an angle of approximately 16 degrees from horizontal (or 74 degrees from the axial centerline) is a preferred configuration for a variety of burn scars. Other attack angles, from a few degrees to up to about 50 degrees from horizontal may be useful in particular situations.

The foregoing description has been presented and is intended for the purposes of illustration and description. It is not intended to be exhaustive nor limit the invention to the above teachings. The embodiments were chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims.

What is claimed is:

1. A microneedling cartridge attachable to a microneedling device for treatment of hypertrophic scars on a surface, having needles that penetrate to different depths and are not perpendicular to the surface, comprising a cartridge body having an axial centerline and a distal end sloped at a predetermined angle, and an array of microneedles that alternately extend from and retract into the cartridge body to penetrate the surface at different depths at the predetermined angle when the microneedling device is operated.

2. The microneedling cartridge of claim 1, further comprising a microneedle platform, an attached microneedle plate sloped at the predetermined angle, and an array of microneedles of equal length extending parallel to the axial centerline of the cartridge body.

3. The microneedling cartridge of claim 1, further comprising a microneedle platform with a distal end sloped at the predetermined angle, an attached microneedle plate sloped at the predetermined angle, and an array of microneedles of equal length extending parallel to the axial centerline of the cartridge body.

4. The microneedling cartridge of claim 1, further comprising a microneedle platform and microneedle plate perpendicular to the axial centerline of the cartridge, and a plurality of microneedles of graduated length such that the needle tips extending from the plate form an array sloped at the predetermined angle.

5. The microneedling cartridge of claim 1 wherein the predetermined angle is between ten degrees and fifty degrees from a plane perpendicular to the axial centerline of the cartridge body.

6. The microneedling cartridge of claim 2 wherein the predetermined angle is between ten degrees and fifty degrees from a plane perpendicular to the axial centerline of the cartridge body.

7. The microneedling cartridge of claim 3 wherein the predetermined angle is between ten degrees and fifty degrees from a plane perpendicular to the axial centerline of the cartridge body.

8. The microneedling cartridge of claim 4 wherein the predetermined angle is between ten degrees and fifty degrees from a plane perpendicular to the axial centerline of the cartridge body.

9. The microneedling cartridge of claim 1 wherein the predetermined angle is approximately sixteen degrees from a plane perpendicular to the axial centerline of the cartridge body.

10. The microneedling cartridge of claim 2 wherein the predetermined angle is approximately sixteen degrees from a plane perpendicular to the axial centerline of the cartridge body.

11. The microneedling cartridge of claim 3 wherein the predetermined angle is approximately sixteen degrees from a plane perpendicular to the axial centerline of the cartridge body.

12. The microneedling cartridge of claim 4 wherein the predetermined angle is approximately sixteen degrees from a plane perpendicular to the axial centerline of the cartridge body.

13. The microneedling cartridge of claim 1 wherein the predetermined angle is sixteen degrees from a plane perpendicular to the axial centerline of the cartridge body.

14. The microneedling cartridge of claim 2 wherein the predetermined angle is sixteen degrees from a plane perpendicular to the axial centerline of the cartridge body.

15. The microneedling cartridge of claim 3 wherein the predetermined angle is sixteen degrees from a plane perpendicular to the axial centerline of the cartridge body.

16. The microneedling cartridge of claim 4 wherein the predetermined angle is sixteen degrees from a plane perpendicular to the axial centerline of the cartridge body.

* * * * *